(12) United States Patent
Filipin

(10) Patent No.: US 11,707,339 B2
(45) Date of Patent: Jul. 25, 2023

(54) DISTANCE INDICATION FOR INVASIVE MICROSURGICAL INSTRUMENTS

(71) Applicant: Alcon Inc., Fribourg (CH)

(72) Inventor: Ivan Filipin, Feuerthalen (CH)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 17/095,829

(22) Filed: Nov. 12, 2020

(65) Prior Publication Data

US 2021/0161610 A1 Jun. 3, 2021

Related U.S. Application Data

(60) Provisional application No. 62/942,792, filed on Dec. 3, 2019.

(51) Int. Cl.
*A61B 90/00* (2016.01)
*A61B 17/00* (2006.01)

(52) U.S. Cl.
CPC .............. *A61B 90/08* (2016.02); *A61B 17/00* (2013.01); *A61B 2017/00022* (2013.01); *A61B 2017/00225* (2013.01); *A61B 2090/0807* (2016.02)

(58) Field of Classification Search
CPC . A61B 90/08; A61B 17/00; A61B 2090/0807; A61B 2017/00022; A61B 2017/00225
USPC ............................................................. 606/1
See application file for complete search history.

(56) References Cited

U.S. PATENT DOCUMENTS

| | | |
|---|---|---|
| 9,730,834 B2 | 8/2017 | Charles |
| 10,500,090 B2 | 12/2019 | Gunn et al. |
| 2005/0149002 A1* | 7/2005 | Wang ...................... A61L 31/18 606/1 |
| 2016/0114112 A1* | 4/2016 | Riebman ............. B05B 11/0078 604/500 |
| 2018/0042768 A1 | 2/2018 | Charles |

* cited by examiner

*Primary Examiner* — Aaron F Roane
(74) *Attorney, Agent, or Firm* — Patterson + Sheridan, LLP

(57) ABSTRACT

A microsurgical instrument having one or more distance indication members is provided. In a particular embodiment, the microsurgical instrument comprises a microsurgical tool and a first distance indication member coupled to, and extending beyond a distal end of, the microsurgical tool. A distal portion of the first distance indication member may be configured to deflect when in contact with a tissue surface, without causing damage to the tissue surface, to give a visual indication that the distal end of the microsurgical tool is in proximity to the tissue surface. The distal portion of the distance indication member can be further configured to return to a non-deflected configuration when no longer in contact with the tissue surface.

19 Claims, 3 Drawing Sheets

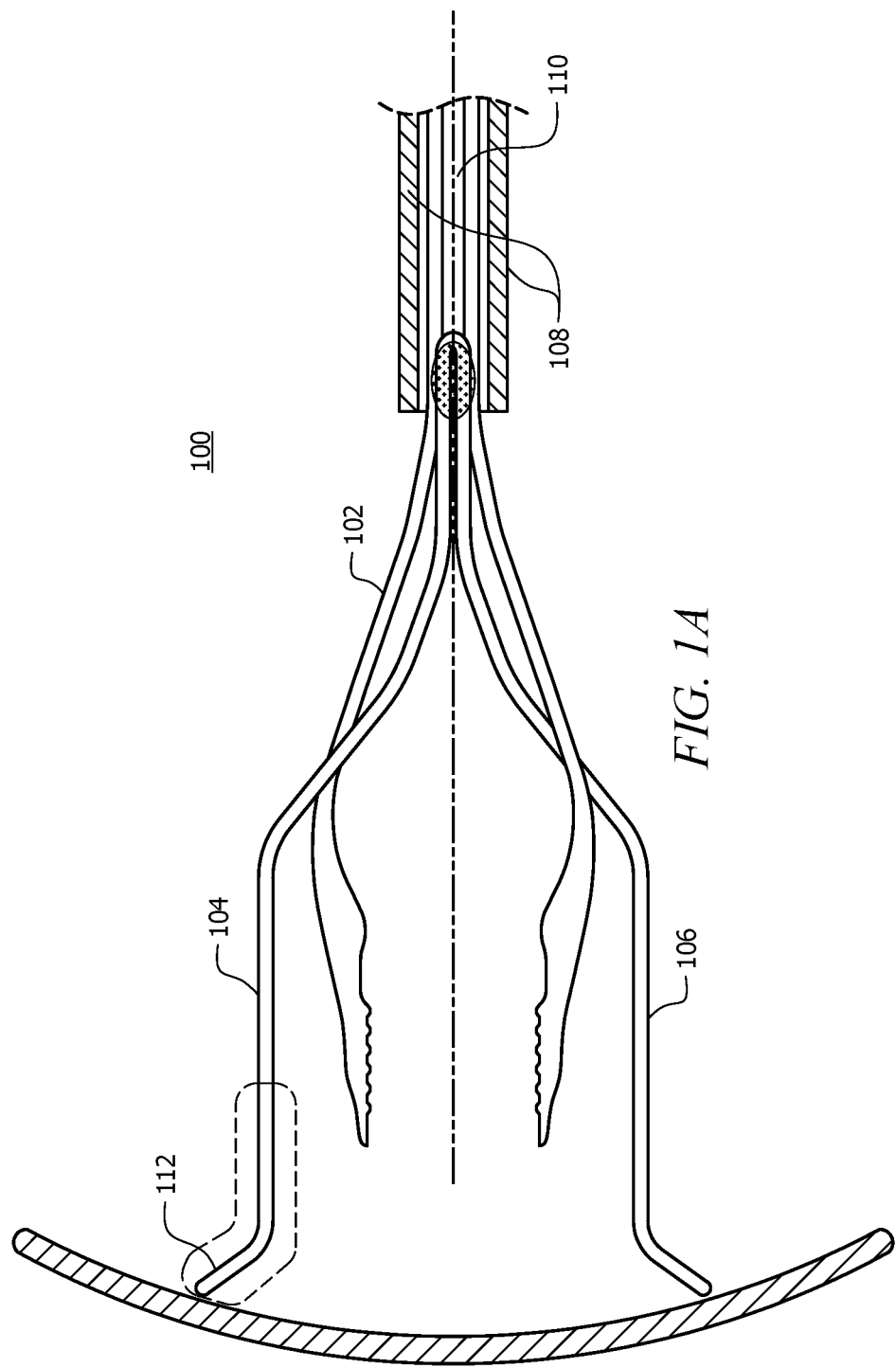

DISTANCE INDICATION FOR INVASIVE MICROSURGICAL INSTRUMENTS

PRIORITY CLAIM

This application claims the benefit of priority of U.S. Provisional Patent Application Ser. No. 62/942,792 titled "DISTANCE INDICATION FOR INVASIVE MICROSURGICAL INSTRUMENTS," filed on Dec. 3, 2019, whose inventor is Ivan Filipin.

TECHNICAL FIELD

The present invention generally relates to the field of microsurgical instruments and, more particularly, to microsurgical instruments having one or more distance indication members.

BACKGROUND OF THE INVENTION

Many microsurgical procedures require precision cutting and/or removal of various body tissues. For example, ophthalmic surgery often requires cutting, removal, dissection, delamination, coagulation, or other manipulation of delicate tissues such as the vitreous humor, traction bands, membranes, and/or the retina. Therefore, cutting, removal, and/or other manipulation of the eye must be done with great care to avoid traction on the retina, the separation of the retina from the choroid, a retinal tear, or, in the worst case, cutting and removal of the retina itself.

Microsurgical instruments, such as vitrectomy probes, fiber optic illuminators, infusion cannulas, aspiration probes, scissors, forceps, and lasers are typically utilized during ophthalmic surgery. These devices are generally inserted through one or more surgical incisions in the sclera near the pars plana and/or via cannulas.

To reduce potential damage to surgical sites and reduce recovery time, care must be taken to avoid inadvertently contacting tissue surfaces such as the retina. Because the operator of the microsurgical instruments is viewing the operation through a microscope or a viewing screen, knowing the depth of an instrument and its distance from a tissue surface may be difficult to ascertain precisely.

BRIEF SUMMARY OF THE INVENTION

In accordance with the teachings of the present invention, a microsurgical instrument comprising a microsurgical tool and at least one distance indication member is provided. In a particular embodiment, the microsurgical tool, such as a forceps or scissors, is operatively positioned within a tubular member. The distal end of the tubular member is coupled to the proximal end of the distance indication member. The distal portion of the distance indication member is located a predetermined distance from the distal end of the tubular member, and is configured to transition from a first, undeflected position of use to a second, deflected position of use when a predetermined force is applied thereto. In this second, deflected position of use, the distal portion is angled relative to the remaining portion of the distance indication member, giving the operator of the instrument a visual indication that the distance indication member has encountered a surface and that the microsurgical tool is in close proximity to the surface.

In another embodiment, the microsurgical instrument comprises a microsurgical tool and a first distance indication member coupled to, and extending beyond a distal end of, the microsurgical tool. A distal portion of the first distance indication member is configured to deflect when in contact with a tissue surface, without causing damage to the tissue surface, to provide the operator a visual indication that the distal end of the microsurgical tool is in proximity to the tissue surface. The distal portion of the distance indication member is further configured to return to a non-deflected configuration when no longer in contact with the tissue surface. In particular embodiments, the microsurgical tool further comprises a second distance indication member coupled to, and extending beyond the distal end of, the microsurgical tool. This second distance indication member also has a distal portion configured to deflect when in contact with the tissue surface, without causing damages to the tissue surface, to provide the operator a visual indication that the distal end of the microsurgical tool is in proximity to the tissue surface, and to return to a non-deflected configuration when no longer in contact with the tissue surface.

One of ordinary skill in the art will appreciate the lengths of the distance indication members in embodiments that employ more than one distance indication member can vary. More specifically, in some applications, the intended tissue of contact may be curved, wherein it may be beneficial to provide the operator indication of curvature by providing distance indication members of different lengths. In other applications, it may be desirous to contact the tissue surface with the first distance indication member initially followed by contact with the second distance indication member, wherein the tip of the first distance indication member would be bent to a greater degree. This aspect of some embodiments of the present invention would allow the operator to fine-tune the initial distance setting to a more preferred spacing from the tissue surface.

The distance indication members may also prevent the distal end of the microsurgical tool from accidentally contacting a tissue surface such as the retina. The distance indication members may provide a warning to the operator of the microsurgical instrument that the distal end of the microsurgical tool is in close proximity to the tissue surface and thereby reduce the likelihood of accidentally contacting the tissue surface with the distal end of the microsurgical tool.

The contemplated distance indication members may be made of any suitable material that is capable of bending upon minimal pressure. In some embodiments, the distance indication member employs a thinned portion that acts as a "living hinge" that facilitates bending. The distance indication member may also possess areas of varying colors or patterns (e.g., stripes, dots) to help the operator better ascertain when the distal portion of the distance indication member is touching or adjacent to the tissue surface. And in a related aspect of some embodiments, the distance indication member, or portions thereof, may be constructed of a piezoelectric material that creates an electrical charge when compressed or bent, which may provide feedback to the operator.

It is one aspect of some embodiments of the present invention to provide a distance indication member made of a material that changes color when compressed or bent, such as chromogenic or piezochromic polymers. Further, the distal portion of the distance indication member may be made of material that provides operator feedback (e.g., a color change) when it contacts tissue or the components thereof (e.g., certain proteins). One of ordinary skill in the art will appreciate that the distance indication member may include one or more of the active indicators or more passive indicators described herein.

It is another aspect of some embodiments of the present invention to provide a distance indication member that dissolves after a predetermined amount of time when exposed to, for example, the fluids of the eye. Preselected portions of the distance indication member may be made of such material, such as the distal portion of the distance indication member.

It is still yet another aspect of some of the embodiments of the present invention described herein to provide a distance indication member that is selectively integrated with the surgical tool and does not affect the operation thereof. Accordingly, the distance indication member or members of some embodiments may be selectively removed from the surgical tool when not needed.

By providing a microsurgical instrument with distance indication members, particular embodiments of the present invention are able to provide enhanced functionality to surgeons. For example, particular embodiments of the present invention may allow a surgeon to accurately determine the distance of the microsurgical tool from the surface of a surgical area, such as a retina. Particular embodiments may also help the surgeon prevent accidental damage to the surgical area due to inadvertent touching of the surgical area by the microsurgical tool.

BRIEF DESCRIPTION OF THE DRAWINGS

The appended figures depict certain aspects of the one or more embodiments of the present invention and are therefore not to be considered limiting of the scope of this disclosure.

FIG. 1A is a top plan view of a microsurgical instrument comprising a forceps and distance indication members in accordance with one embodiment of the present invention.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

In accordance with the teachings of the present invention, a microsurgical instrument comprising a microsurgical tool and at least one distance indication member is disclosed. In a particular embodiment, the microsurgical tool, such as a forceps or scissors, is operatively positioned within a tubular member. The distal end of the tubular member is coupled to the proximal end of the distance indication member. The distal portion of the distance indication member is located a predetermined distance from the distal end of the tubular member, and is configured to transition from a first, undeflected position of use to a second, deflected position of use when a predetermined force is applied thereto. In this second, deflected position of use, the distal portion is angled relative to the remaining portion of the distance indication member, giving the operator of the instrument a visual indication that the distance indication member has encountered a surface and that the microsurgical tool is in close proximity to the surface.

In another embodiment, the microsurgical instrument comprises a microsurgical tool and a first distance indication member coupled to, and extending beyond a distal end of, the microsurgical tool. A distal portion of the first distance indication member is configured to deflect when in contact with a tissue surface, without causing damage to the tissue surface, to provide the operator a visual indication that the distal end of the microsurgical tool is in proximity to the tissue surface. The distal portion of the distance indication member is further configured to return to a non-deflected configuration when no longer in contact with the tissue surface. In particular embodiments, the microsurgical tool further comprises a second distance indication member coupled to, and extending beyond the distal end of, the microsurgical tool. This second distance indication member also has a distal portion configured to deflect when in contact with the tissue surface, without causing damages to the tissue surface, to provide the operator a visual indication that the distal end of the microsurgical tool is in proximity to the tissue surface, and to return to a non-deflected configuration when no longer in contact with the tissue surface.

By providing a microsurgical instrument with distance indication members, particular embodiments of the present invention are able to provide enhanced functionality to surgeons. For example, particular embodiments of the present invention may allow a surgeon to accurately determine the distance of the microsurgical tool from the surface of a surgical area, such as a retina. Particular embodiments may also help the surgeon prevent accidental damage to the surgical area due to inadvertent touching of the surgical area by the microsurgical tool.

Figure 1B:
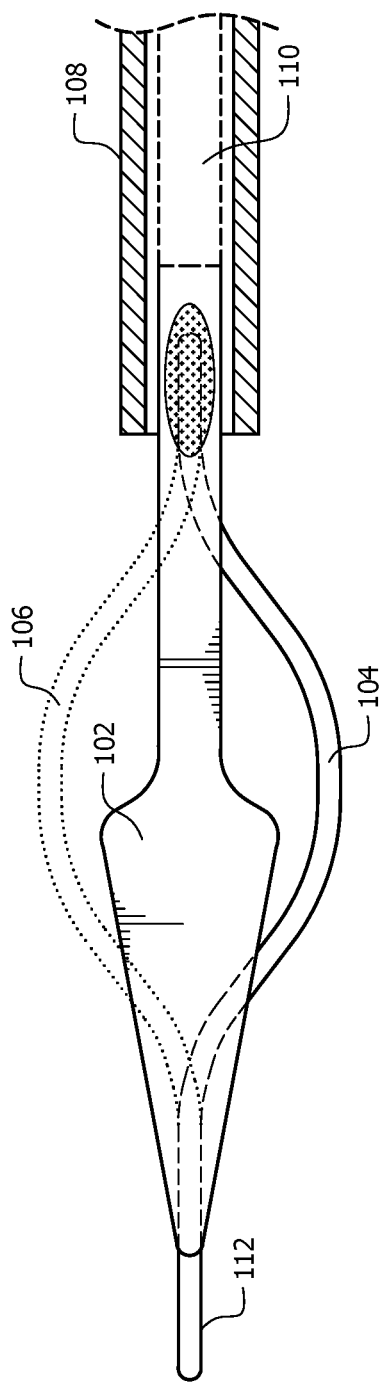
FIG. 1B is a side elevation view of the microsurgical instrument shown in FIG. 1A.

FIGS. 1A and 1B illustrate a microsurgical instrument 100 comprising a set of forceps 102 with two distance indication members, 104 and 106, respectively. Although FIGS. 1A and 1B illustrate forceps 102, other microsurgical tools are also contemplated within the teachings of the present invention, including but not limited to scissors, scrapers, spatulas, scalpels, diathermy probes, vitrectomy probes, fiber optic illuminators, infusion cannulas, aspiration probes, and laser probes. The distance indication members 104 and 106 are sometimes referred to herein as upper distance indication member 104 and lower distance indication member 106. FIG. 1A shows two distance indication members but any number of distance indication members may be employed. FIG. 1A illustrates the forceps 102 in an expanded position in a top-down view from a position orthogonal to the plane in which the forceps 102 open. FIG. 1B illustrates the forceps 102 in a side view from the plane in which the forceps 102 open.

As shown in FIGS. 1A and 1B, microsurgical instrument 100 includes a tubular member 108 with a shaft 110 coaxially extending therethrough. Forceps 102 are coupled to shaft 100 and actuated by the movement of tubular member 108 through movement of the shaft 110 within and relative to tubular member 108.

In particular embodiments, distance indication members 104 and 106 are attached to forceps 102, wherein at least a portion of the distance indication members 104 and 106 extend beyond the distal end of the forceps 102. In some embodiments, the upper distance indication member 104 and the lower distance indication member 106 may be coupled to inner portions of the arms of the forceps 102. Alternatively, distance indication members 104 and 106 may be coupled to outer portions of the forceps 102. In other embodiments, distance indication members 104 and 106 may be coupled directly to the shaft 110. And in yet other embodiments, distance indication members 104 and 106 may be coupled to tubular member 108, for example, in embodiments where forceps 102 is be fixed in relation to the tubular member 108.

In particular embodiments, tubular member 108 may be made of a metal or another substantially rigid material. The tubular member 108 may be designed to penetrate the eye or inserted into a small cannula (e.g., smaller than 20 gauge) that has penetrated the eye so that the forceps 102 and distance indication members 104, 106 can reach the surgical site. In some examples, distance indication members 104, 106 may be relatively small. For example, in some embodiments, distance indication members 104, 106 may each have a width within a range of about 0.05 to 0.3 mm. Other sizes, both larger and smaller, are contemplated within the teachings of the present disclosure.

The distance indication members 104 and 106 are configured to provide a visual indication to the operator of the microsurgical instrument 100 that the distal end of the forceps 102 are approaching a tissue surface, such as a retina, before the distal end of the forceps 102 contact the tissue surface. In general, the distance indication member may extend a greater distance than the distal end of the microsurgical tool along any axis to provide a visual distance indication to the operator of the microsurgical instrument 100. In particular embodiments, upper distance indication member 104 and lower distance indication member 106 may extend the same distance beyond the distal end of forceps 102 as each other (as measured along the longitudinal axis of the surgical tool). For example, in a particular embodiment upper and lower distance indication members 104 and 106 may extend about 0.3 to 1.0 mm beyond the distal end of the forceps 102. In another embodiment, distance indication members 104, 106 may extend about 0.5 to 0.8 mm beyond the distal end of forceps 102. And, in yet another embodiment, distance indication members 104, 106 may extend about 0.6 mm beyond the distal end of forceps 102. Other suitable distances may be readily ascertained by persons of ordinary skill with the benefit of the present disclosure.

In other embodiments, upper distance indication member 104 may extend a first distance beyond the distal end of forceps 102, whereas lower distance indication member 106 extends a second, different distance beyond the distal end of forceps 102. In such an embodiment, upper and lower distance indication members 104 and 106 may each provide a graduated, or staged, indication of the proximity of forceps 102 to the tissue surface. For example, in a particular embodiment upper distance indication member 104 may extend about 0.6 to 1.0 mm beyond the distal end of forceps 102, while lower distance indication member 106 may extend about 0.3 to 0.6 mm beyond the distal end of forceps 102. In another embodiment, upper distance indication member 104 may extend about 1.0 mm beyond the distal end of forceps 102, while lower distance indication member 106 may extend about 0.5 mm beyond the distal end of forceps 102. Again, other suitable distances may be readily ascertained by persons of ordinary skill with the benefit of the present disclosure.

In general, the upper and lower distance indication members 104 and 106 also provide sufficient radial clearance for the microsurgical tool, so as not to interfere with the operation of the tool (e.g., the opening and closing of the forceps). The specific amount of radial clearance provided by the distance indication members 104 and 106 may vary depending on the specific type of microsurgical tool employed. However, the appropriate amount of radial clearance may be readily ascertained by persons of ordinary skill with the benefit of this disclosure.

In other embodiments, different configurations in the location and shape of distance indication members 104, 106 could be employed. For example, rather than using two distance indication members (e.g., upper and lower distance indication members 104 and 106) a single distance indication member could be used. Similarly, three or more distance indication members could be used. In addition, the orientation of the distance indication member(s) could be modified. For example, the distance indication members 104 and 106 could be located coplanar or orthogonal with the arms of the forceps 102. In one example, shown in FIG. 1B, upper distance indication member 104 may be curved above the plane in which the forceps 102 open and close, whereas lower distance indication member 106 is shown to curve below the plane in which the forceps 102 open and close. In such an embodiment, this allows the forceps 102 to open and close with minimal, or at least reduced, interference from upper and lower distance indication members 104 and 106, respectively.

In general, distance indication members 104 and 106 are configured to contact and interface with a tissue surface such as a retina. As the distal end of the microsurgical tool approaches the tissue surface, a portion of the distance indication member 104, 106 initially contacts the tissue surface and moves, or deflects, from a first position of use to a second position of use. The operator of the microsurgical tool provides the necessary force to position the microsurgical tool closer to the tissue surface and to deflect the distance indication member 104, 106 from the first position to the second position. Deflection of the distance indication member 104, 106 into the second position provides the operator of the microsurgical instrument 100 the visual indication of the distance from the distal end of the microsurgical tool to the tissue surface. The force necessary to cause the deflection of the distance indication member 104, 106 can be predetermined and differing levels of force may produce different levels of deflection by the distance indication member 104, 106. Once a distance indication member 104, 106 is removed from contact with the tissue surface, the distance indication member 104, 106 will return to the non-deflected, first position of use.

The distance indication members 104, 106 may assume many possible configurations when contacting the tissue surface. In one example, as shown in FIG. 1A, the distal portion 112 of a distance indication member 104 is angled. As also shown in FIG. 1A, the majority of a distance indication member 104 is substantially parallel to the longitudinal axis of the microsurgical tool and, thus, much of the distance indication member 104 would not be readily visible to the microsurgical instrument operator when the distance indication member 104 is not in contact with a tissue surface. The angle of the distal portion 112 of distance indication member 104 forces the distal portion 112 of the distance indication member 104 to spread outwardly from the longitudinal axis of the microsurgical tool when the distance indication member 104 contacts the tissue surface. As the operator moves the distal end of the microsurgical tool (e.g., forceps 102) closer to the tissue surface, the deflection of the distance indication member 104 will increase and the distal portion 112 of distance indication member 104 will become more visible to the operator. Thus, in this configuration, the amount the distance indication member 104 readily visible to the operator is related to the distance the distal end of the microsurgical tool is from the tissue surface—the closer the microsurgical tool is to the tissue surface, the greater the amount of distance indication member 104 that will be readily visible to the user. When the microsurgical tool is moved away from the tissue surface, the distal portion 112 of the distance indication member 104 will return to a non-deflected configuration and the operator will know the microsurgical tool is no longer in contact with the tissue surface.

In another possible configuration, the distal portion 112 of a distance indication member 104 will not spread outwardly when it contacts the tissue surface, but rather the distal portion 112 of a distance indication member 104 remains stationary and at least an intermediate portion of the distance indication member 104 (e.g., between the distal and proximal ends of the member) deflects, or bows out, to provide the visual distance indication to the operator regarding the proximity of the microsurgical tool to the tissue surface.

In particular embodiments, distance indication members 104, 106 may be formed of a flexible material. Because the distance indication members 104, 106 are intended to contact sensitive tissue surfaces (e.g., the retina), the material may be extremely flexible to avoid damaging sensitive tissue surfaces within the eye. The material can also possess considerable elasticity to resume the desired shape after microsurgical tool 100 is compressed to pass through a cannula. Suitable materials for distance indication members 104, 106 may include EPDM (ethylene-propylene-diene monomer rubber), PHA (poly-hydroxy-alkanoate), and/or PHB (poly-hydroxy-butyrate). In particular embodiments, distance indication members 104, 106 may comprise a material that dissolves after a predetermined amount of time when exposed to, for example, the fluids of the eye. Such a material could prevent contamination of the eye if portions of distance indication members 104, 106 broke off, or were separated from, the microsurgical instrument 100 during surgery. Preselected portions of distance indication members 104, 106 may be made of such materials, such as the distal portion 112 of distance indication member 104.

In particular embodiments, distance indication members 104, 106 may employ a thinned or narrowed portion that acts as a "living hinge" that facilitates bending of the distance indication members 104, 106. The thinned or narrowed portion of the distance indication members 104, 106 could be more prone to bending than the remaining portions of the distance indication members 104, 106 in order to facilitate bending of the distance indication members 104, 106 in a prescribed manner. Other materials that provide the desired flexibility, elasticity, and visibility that may be used as well would be known to a person of skill in the art with the benefit of this disclosure.

The distance indication members 104, 106 may also be designed to be capable of being easily seen by an operator of the microsurgical instrument 100. For example, in particular embodiments, the distance indication members 104, 106 may be a color, such as green, that enhances visibility relative to the tissue surface. Similarly, the distance indication members 104, 106 may be covered with a visual pattern, such as stripes or dots that enhances visibility. In particular embodiments, the color or visual markings on the distance indication members 104, 106 may differ at different points on the member to give the operator more discrete information about the proximity of the distal end of the microsurgical tool (e.g., forceps 102) to the tissue surface. For example, a distal portion 112 of distance indication member 104 may be green, an intermediate portion may be yellow, and a more proximal portion may be red. As the distance indication member 104 deflects outward, the green will first become visible to the operator, followed by the yellow as the microsurgical tool advances closer to the tissue surface, followed by the red as the microsurgical tool advances even closer to the tissue surface. In particular embodiments, portions of distance indication members 104, 106 may be enlarged in area to aid the operator of the microsurgical instrument 100 to view the distance indication members 104, 106.

In particular embodiments, distance indication members 104, 106 may be designed of materials capable of providing additional feedback to an operator of the microsurgical instrument 100. It is one aspect of some embodiments of the present invention to provide distance indication members 104, 106 made of material that changes color when compressed or bent, such as chromogenic or piezochromic polymers. Such a material would allow an operator to determine by the color change of the distance indication members 104, 106 the amount of force being applied to the distance indication members 104, 106 by the operator and may highlight to the operator that the distance indication members 104, 106 have been deflected. Further, the distal portion 112 of the distance indication members 104, 106 may be made of material that provides operator feedback (e.g., a color change) when it contacts tissue or the components thereof (e.g., certain proteins). Such a material would allow an operator to determine by the color change of the distance indication members 104, 106 the type of surface in contact with the distance indication members 104, 106. In particular embodiments, the distance indication members 104, 106, or portions thereof, may be constructed of a piezoelectric material that creates an electrical charge when compressed or bent. This electrical charge could be utilized to provide feedback to the operator through a surgical console or through the microsurgical instrument 100. One of ordinary skill in the art will appreciate that the distance indication members 104, 106 may include one or more of the active indicators or more passive indicators described herein.

There are a variety of possible configurations of distance indication members 104 that could be implemented for a given microsurgical instrument 100. Generally, the distance indication member 104 may surround the microsurgical tool (e.g., forceps 102) with a three-dimensional structure that exceeds the length and width of the microsurgical tool without impairing the intended functionality of the microsurgical tool. The design of distance indication members 104, 106 may provide an operator with an accurate visual distance indication from a tissue surface while not damaging the tissue surface through contact by distance indication members 104, 106 while meeting the mechanical requirement of being able to be retracted to fit through a small incision or cannula.

Figure 2A:
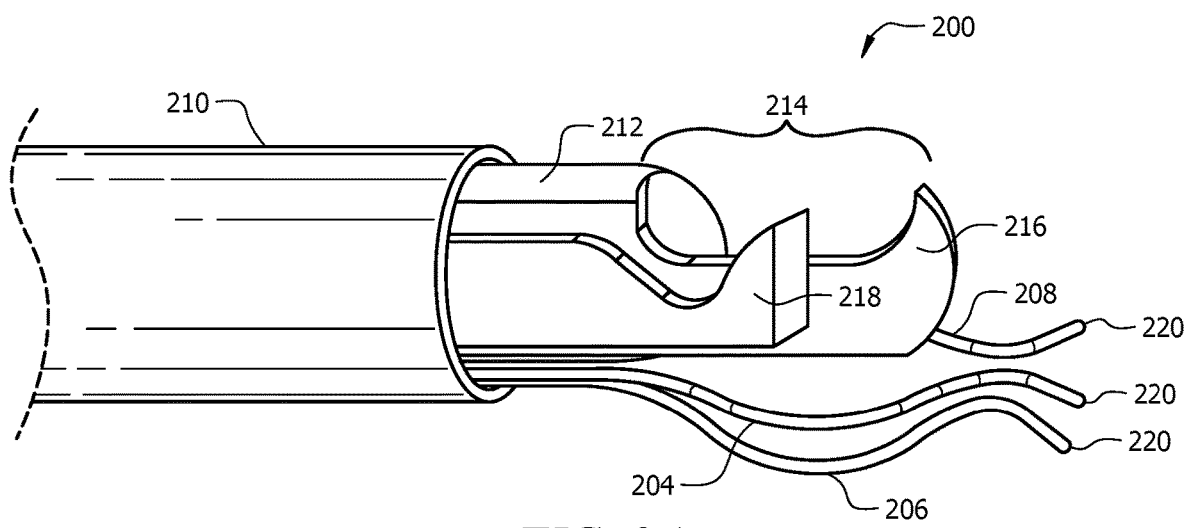
FIG. 2A is a side elevation of a microsurgical instrument comprising a probe with scissors functionality and distance indication members in accordance with one embodiment of the present invention.
Figure 2B:
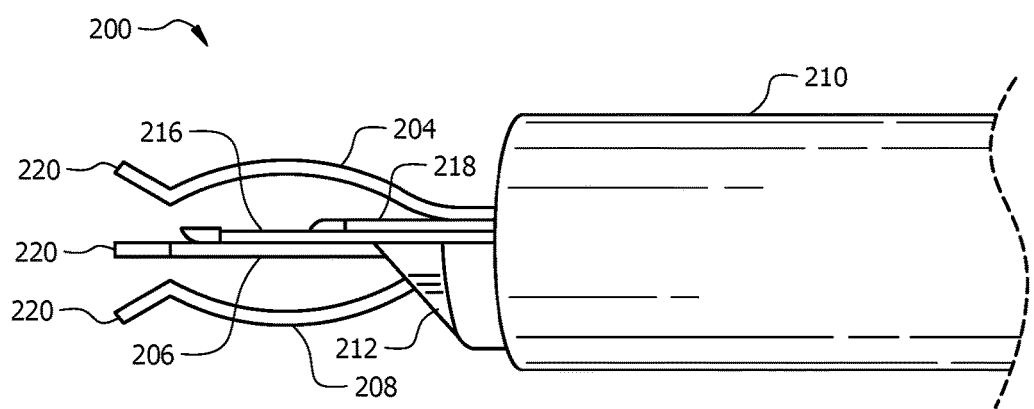
FIG. 2B is a top plan view of the microsurgical instrument shown in FIG. 2A.

FIGS. 2A and 2B illustrate a microsurgical instrument 200 in accordance with another embodiment of the present invention. FIGS. 2A and 2B illustrate microsurgical instrument 200 comprising scissors 214 and three distance indication members 204, 206, and 208. FIG. 2A illustrates the microsurgical instrument 200 in a side view orthogonal to the plane in which scissors 214 open, while FIG. 2B illustrates microsurgical instrument 200 in a top-down view parallel to the plane in which scissors 214 open. Although FIG. 2A illustrates three distance indication members, one of ordinary skill in the art, with the benefit of this disclosure, should appreciate that any number of distance indication members may be employed without departing from the teachings of the present disclosure.

As shown in FIGS. 2A and 2B, scissors 214 comprises a first blade 216 and a second blade 218, and may be at least partially received within a tubular member 210. In particular embodiments, first blade 216 may be fixed relative to the tubular member 210, e.g., by welding, while second blade 218 may be configured to move longitudinally within the tubular member 210, relative to the first blade 216.

Microsurgical instrument 200 also includes a shaft 212 that extends coaxially through tubular member 210. In particular embodiments, shaft 212 may be used as an attachment point for distance indication members 204, 206, and 208. For example, first distance indication member 204 and third distance indication member 208 are shown attached to shaft 212 in a coplanar manner, whereas second distance indication member 206 is attached to a shaft 212 orthogonal to the plane in which distance indication members 204 and 208 are attached. Other possible attachment points, such as the outer portions of the scissors 214 or portions of the tubular member 210, as also possible within the teachings of the present invention, provided that the distance indication members should be attached in such a manner that the distance indication members extend further than the distal end of the microsurgical tool (e.g., scissors 214) to which they are coupled.

Similar to the distance indication members 104 and 106 described above with respect to FIGS. 1A and 1B, distance indication members 204, 206, and 208 are configured to provide the operator of microsurgical instrument 200 with a visual indication that scissors 214 is in close proximity to a tissue surface. For example, as also shown in FIG. 2A, the majority of a distance indication member 204 is substantially parallel to the longitudinal axis of microsurgical instrument 200 and, thus, much of the distance indication member 204 would not be readily visible to the microsurgical instrument operator when the distance indication member 204 is not in contact with a tissue surface. However, the distal portion 220 of distance indication member 204 is angled slightly outward. When the distal portion 220 of the distance indication member 204 contacts the tissue surface, the angle of the distal portion 220 of distance indication member 204 forces the distance indication member 204 to spread outwardly from the longitudinal axis of microsurgical instrument 200. As the operator moves the distal portion 220 of scissors 214 closer to the tissue surface, the deflection of the distance indication member 204 will increase and the distal portion 220 of the member will be more readily visible to the operator. Thus, in this configuration, the greater the amount of distance indication member 204 that is readily visible to the operator, the closer the distal end of scissors 214 is to the tissue surface. When scissors 214 is moved away from the tissue surface, the distal portion 220 of the distance indication member 204 is configured return to a non-deflected configuration, thus giving the operator a visual indication that scissors 214 is no longer in close proximity to the tissue surface. Distance indication members 206 and 208 may be configured similarly to distance indication member 204.

In another possible configuration, the distal portion 220 of the distance indication members 204, 206 and 208 will not spread outwardly when they contact the tissue surface. Instead, the distal portions 220 of distance indication members 204, 206, and 208 may remain stationary and an intermediate portion of each distance indication member 204, 206 and 208 (between the distal portion and a more proximal portion), may deflect, or bow out, to provide the visual indication to the operator regarding the proximity of the microsurgical tool (e.g., scissors 214) to the tissue surface.

In particular embodiments, the distal portions 220 of distance indication members 204, 206, and 208 extend beyond the distal end of scissors 214 by a predetermined amount. For example, in a particular embodiment distance indication members 204, 206, and 208 extend beyond the distal end of scissors 214 by about 0.2 to 0.7 mm. In another embodiment, distance indication members 204, 206, and 208 may extend about 0.5 mm beyond the distal end of scissors 214. In other embodiments, the distance indication members may extend a greater or smaller distance beyond the distal end of scissors 214. In FIGS. 2A and 2B, distance indication members 204, 206 and 208 are also shown having the same length. However, in particular embodiments, distance indication members 204, 206, and 208 may each have a different length. Moreover, in some embodiments, distance indication members 204, 206, and 208 may be easily frangible or include perforated or thinned areas that allow the operator to selectively reduce the length of each distance indication member individually. Providing a microsurgical instrument 200 with distance indication members 204, 206, 208 of different lengths may increase the accuracy of the visual distance indication to the operator regarding the depth of the microsurgical instrument 200.

Distance indication members 204, 206, and 208, are also positioned with sufficient radial clearance around scissors 214 so as not to interfere with the operation of scissors 214. The amount of radial clearance between the distance indication members 204, 206, and 208 and scissors 214 that is sufficient for a particular embodiment may be readily ascertained by persons of ordinary skill with the benefit of this disclosure.

Because distance indication members 204, 206, and 208 are intended to contact and interface with a sensitive tissue surface, such as a retina, distance indication members 204, 206, and 208 are designed to be capable of touching the tissue surface without damaging it. For example, distance indication members 204, 206, and 208 are formed of a flexible material to avoid damaging sensitive tissue surfaces within the eye. The material can also possess considerable elasticity to resume the desired shape once a distance indication member 204 is passed through an entry cannula to gain access to the interior of an eye. In particular embodiments, the distance indication members 204, 206, and 208 may be made of EPDM (ethylene-propylene-diene monomer rubber), PHA (poly-hydroxy-alkanoate), and/or PHB (poly-hydroxy-butyrate). Other materials that provide the desired flexibility, elasticity, and visibility that may be used as well would be known to a person of skill in the art with the benefit of this disclosure.

In particular embodiments, distance indication members 204, 206, and/or 208 may also be comprised of a material that dissolve after a predetermined amount of time when exposed to, for example, the fluids of the eye. Such a material could prevent contamination of the eye if portions of one of the distance indication members 204, 206, and/or 208 broke off or were separated from the microsurgical instrument 200 during surgery. Preselected portions of the distance indication members 204, 206, and/or 208 may be made of such materials, such as the distal portion 220.

The distance indication members 204, 206, and 208 may also be designed to be capable of being easily seen by an operator of the microsurgical instrument 200. For example, in particular embodiments, the distance indication members 204, 206, and 208 may be a color, such as green, that enhances the visibility of the member relative to the tissue surface. Similarly, the distance indication members 204, 206, and 208 may be covered with a visual pattern, such as stripes or dots that enhances visibility. In particular embodiments, the color or visual markings on the distance indication members 204, 206, and 208 may differ at different points on the members to give the operator more discrete information about the proximity of the distal end of the microsurgical tool to the tissue surface. For example, a distal portion 220 of distance indication member 204 may be green, an intermediate portion may be yellow, and a more proximal portion may be red. As the distance indication member 204 deflects outward, the green will become visible first to the operator, followed by the yellow as the microsurgical tool advances closer to the tissue surface, followed by the red as the microsurgical tool advances even closer to the tissue surface. In particular embodiments, portions of distance indication members 204, 206, and/or 208 may be enlarged in area to be more visible to the operator of the microsurgical instrument 200.

In particular embodiments, distance indication members 204, 206, and/or 208 may comprise materials capable of providing additional feedback to the operator of the instrument. For example, distance indication members 204, 206, and/or 208 may made of a material that changes color when compressed or bent, such as chromogenic or piezochromic polymers. Such a material would allow an operator to determine by the color change the amount of force being applied to the distance indication members 204, 206, and/or 208 and may highlight to the operator that the distance indication members 204, 206, and/or 208 have been deflected. Further, the distal portion 220 of the distance indication members 204, 206, and/or 208 may be made of material that provides operator feedback (e.g., a color change) when it contacts tissue or the components thereof (e.g., certain proteins). Such a material would allow an operator to determine by the color change of the distance indication members 204, 206, and/or 208 the type of surface in contact with the distance indication members. In particular embodiments, the distance indication members 204, 206, and/or 208 (or portions thereof) may be constructed of a piezoelectric material that creates an electrical charge when compressed or bent. This electrical charge could be utilized to provide feedback to the operator through a surgical console or through the microsurgical instrument 200. One of ordinary skill in the art will appreciate that the distance indication members 204, 206, and/or 208 may include one or more of the active indicators or more passive indicators described herein.

By providing a microsurgical instrument with distance indication members, particular embodiments of the present invention are able to provide enhanced functionality to surgeons. For example, particular embodiments of the present invention may allow a surgeon to accurately determine the distance of the microsurgical tool from the surface of a surgical area, such as a retina. Particular embodiments may also help the surgeon prevent accidental damage to the surgical area due to inadvertent touching of the surgical area by the microsurgical tool.

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

What is claimed is:

1. A microsurgical instrument, comprising:
   a tubular member;
   a microsurgical tool operatively positioned within the tubular member; and
   a first distance indication member having a proximal end coupled to a distal end of the tubular member;
   wherein a distal portion of the first distance indication member is located a predetermined distance from a distal end of the microsurgical tool;
   wherein the distal portion of the first distance indication member is configured to transition from a first position of use to a second position of use when a predetermined force is applied thereto; and
   wherein the microsurgical instrument is configured to pass through a cannula smaller than 20 gauge.

2. The microsurgical instrument of claim 1, wherein the distal portion of the first distance indication member is further configured to return to the first position of use when the predetermined force is removed.

3. The microsurgical instrument of claim 1, wherein the microsurgical tool is selected from the group consisting of forceps, scissors, scrapers, spatulas, scalpels, diathermy probes, vitrectomy probes, fiber optic illuminators, infusion cannulas, aspiration probes, and laser probes.

4. The microsurgical instrument of claim 1, wherein the distal portion of the first distance indication member comprises EPDM (ethylene-propylene-diene monomer rubber), PHA (poly-hydroxy-alkanoate), or PHB (poly-hydroxy-butyrate).

5. The microsurgical instrument of claim 1, wherein the distal portion of the first distance indication member comprises a color that differs from a remaining portion of the first distance indication member.

6. The microsurgical instrument of claim 1, further comprising:
   a second distance indication member having a proximal end coupled to the distal end of the tubular member and a distal portion located a predetermined distance from the distal end of the tubular member;
   wherein the distal portion of the second distance indication member is configured to transition from a first position of use to a second position of use when a predetermined force is applied thereto.

7. The microsurgical instrument of claim 6, wherein a length of the first distance indication member is unequal to a length of the second distance indication member.

8. A microsurgical instrument, comprising:
   a microsurgical tool; and
   a first distance indication member having a proximal end coupled to the microsurgical tool;
   wherein a distal portion of the first distance indication member is located a predetermined distance from a distal end of the microsurgical tool;
   wherein the distal portion of the first distance indication member is configured to transition from a first position of use to a second position of use when a predetermined force is applied thereto; and
   wherein the microsurgical instrument is configured to pass through a cannula smaller than 20 gauge.

9. The microsurgical instrument of claim 8, wherein the distal portion of the first distance indication member is angled relative to a remaining portion of the first distance indication member.

10. The microsurgical instrument of claim 8, wherein the distal portion of the first distance indication member is further configured to return to the first position of use when the predetermined force is removed.

11. The microsurgical instrument of claim 8, wherein the distal portion of the first distance indication member is a first color when in the first position of use and a second color when in the second position of use.

12. The microsurgical instrument of claim 8, wherein the distal portion of the first distance indication member comprises EPDM (ethylene-propylene-diene monomer rubber), PHA (poly-hydroxy-alkanoate), or PHB (poly-hydroxy-butyrate).

13. The microsurgical instrument of claim 8, wherein the distal portion of the first distance indication member comprises visual markings selected from the group consisting of dots and stripes.

14. The microsurgical instrument of claim 8, further comprising a second distance indication member having a proximal end coupled to the microsurgical tool;
wherein a distal portion of the second distance indication member is located a predetermined distance from the distal end of the microsurgical tool; and
wherein the distal portion of the second distance indication member is configured to transition from a first position of use and a second position of use when a predetermined force is applied thereto.

15. The microsurgical instrument of claim 14, wherein a length of the first distance indication member is unequal to a length of the second distance indication member.

16. A microsurgical instrument, comprising:
a microsurgical tool;
a first distance indication member coupled to, and extending beyond a distal end of: the microsurgical tool;
wherein a distal portion of the first distance indication member is configured to deflect when in contact with a tissue surface to give a visual indication that the distal end of the microsurgical tool is in proximity to the tissue surface;
wherein the distal portion is further configured to return to a non-deflected configuration when no longer in contact with the tissue surface; and
wherein the microsurgical instrument is configured to pass through a cannula smaller than 20 gauge.

17. The microsurgical instrument of claim 16, further comprising:
a second distance indication member coupled to, and extending beyond a distal end of the microsurgical tool;
wherein a distal portion of the second distance indication member is configured to deflect when in contact with the tissue surface to give a visual indication that the distal end of the microsurgical tool is in proximity to the tissue surface; and
wherein the distal portion of the second distance indication member is further configured to return to a non-deflected configuration when no longer in contact with the tissue surface.

18. The microsurgical instrument of claim 16, wherein the microsurgical tool is selected from the group consisting of forceps, scissors, scrapers, spatulas, scalpels, diathermy probes, vitrectomy probes, fiber optic illuminators, infusion cannulas, aspiration probes, and laser probes.

19. The microsurgical instrument of claim 16, wherein the distal portion of the first distance indication member comprises EPDM (ethylene-propylene-diene monomer rubber), PHA (poly-hydroxy-alkanoate), or PHB (poly-hydroxy-butyrate).

* * * * *